United States Patent [19]

Kimura et al.

[11] Patent Number: 4,956,364
[45] Date of Patent: Sep. 11, 1990

[54] NOOTROPIC AGENT

[75] Inventors: Kiyoshi Kimura, Takatsuki; Yojiro Ukai, Kusatsu; Takashi Ogasawara, Uji; Yutaka Nakagawa, Otsu, all of Japan

[73] Assignee: Nippon Shinyaku Co., Ltd., Japan

[21] Appl. No.: 290,050

[22] PCT Filed: Apr. 7, 1988

[86] PCT No.: PCT/JP88/00347
§ 371 Date: Dec. 6, 1988
§ 102(e) Date: Dec. 6, 1988

[87] PCT Pub. No.: WO88/07867
PCT Pub. Date: Oct. 20, 1988

[51] Int. Cl.$^5$ .............................. A61K 31/535
[52] U.S. Cl. ................................. 514/227.5
[58] Field of Search ........................ 514/227.5

[56] References Cited
PUBLICATIONS
Chem. Abst. 101-123206h (1984).

Primary Examiner—Stanley J. Friedman
Attorney, Agent, or Firm—Jacobs & Jacobs

[57] ABSTRACT

The present invention provides a novel nootropic agent which is applicable to senile dementia, etc.

As a nootropic agent, for example, TRH (Thyrotropin releasing hormone) is hitherto known but involves defects that TRH is rapidly decomposed in vivo and, in its nature, cannot be orally administered.

The nootropic agent in accordance with the present invention comprises as a main ingredient the substance having the following chemical structure:

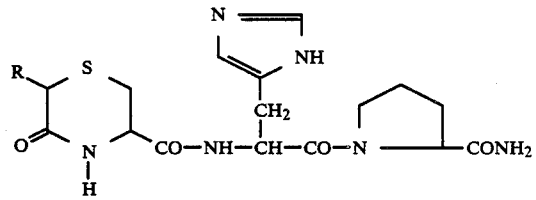

wherein R represents a lower alkyl group.

The effect on animals is remarkable and the toxicity is low. Therefore, the compounds of the present invention are expected to be utilized as drugs. When the society is considered to go toward advanced age, a great weight should be put on treatment of diseases in old age and medical significance of the present invention is extremely important.

8 Claims, No Drawings

NOOTROPIC AGENT

FIELD OF THE INVENTION

The present invention relates to a nootropic agent comprising a histidylprolinamide derivative as a main ingredient.

The histidylprolinamide derivative in accordance with the present invention can be represented by the following general formula [I].

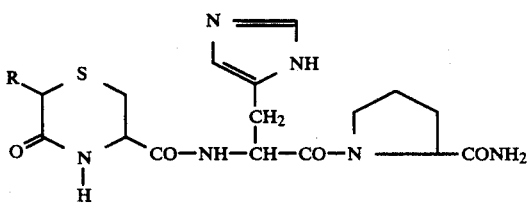

where in R represents a lower alkyl group.

BACKGROUND OF THE INVENTION

As the population of aged persons increases, sinile dementia has been a serious problem but its therapy has not yet been established. Drug therapy by administration of a cerebral metabolism activator, a cerebral blood flow improving agent, a tranquillizer, a cholinergic agent, etc. has been attempted heretofore but its effect is not satisfactory and a new therapeutic agent has been desired in this field.

Recently, some compounds such as Aniracetam, Pramiracetam, etc. have been developed as nootropic agents but are not yet satisfactory in terms of their effects.

In Published Unexamined Japanese Patent Application No. 52-125166 etc.,TRH (Thyrotropin releasing hormone) compounds are disclosed and studies on nootropic activity of TRH have been advanced in these years.

It has been considered that TRH is principally a hormone for regulating release of thyrotropin (TSH) in pituitary gland of mammals. According to recent studies, however, it has been made clear that TRH not only releases TSH but . also widely exists in the central nervous system and possesses various activities [Ann. Rev. Pharmacol. Toxicol., 26, 311-322 (1986)].

It was known that TRH showed various useful activities and could be a useful medicine as a nootropic agent. It was also known that TRH was relatively rapidly decomposed in vivo and its penetration into the brain was not so good. Besides, it can be said that the activity itself of TRH is not so potent as expected and it has been demanded to develop derivatives having a more potent activity.

In addition, the effect of TRH cannot be expected by oral administration in its nature, which is a serious defect as a drug.

On the other hand, investigations have been made on histidylprolinamide derivatives including the compounds of the present invention which are known compounds as substances having an effective pharmacological activity; for example, these derivatives have been attempted to utilize as drugs for treating traumatic neurosis (Published Unexamined Japanese Patent Application No. 61-172828). However, no attempt has been made to investigate the compounds of the present invention by specifying them to specific pharmacological activity, thereby leading to materialization of some new drugs.

DISCLOSURE OF THE INVENTION

In view of the foregoing actual situation, the present inventors have made extensive investigations on the limited compounds of the present invention. As a result, it has been confirmed that the compounds represented by the general formula [I]described above have much more excellent nootropic activity on mammals than TRH and the present invention has come to be accomplished.

As described above, the compounds of the present invention are known and it has been made clear that the compounds have pharmacological activities other than the nootropic activity. However, as will be later described in detail, such an excellent nootropic activity in accordance with the present invention that the activity is sufficiently exhibited even by oral administration has been found by the present inventors for the first time and this is an important feature of the present invention.

The compounds of the present invention can be represented by the general formula [I]described above. As R in [I], mention may be made of a lower alkyl group such as methyl, ethyl, propyl, etc.

Examples of the compounds of the present invention include the following compounds.

6-Methyl-5-oxo-3-thiomorpholinylcarbonylhistidyl-prolinamide

6-Ethyl-5-oxo-3-thiomorpholinylcarbonylhistidyl-prolinamide

6-Propyl-5-oxo-3-thiomorpholinylcarbonylhistidyl-prolinamide

Hereafter pharmacological activities and toxicity of the compounds of the present invention will be described below in detail. In the following experiments, (3R,6R)-6-methyl-5-oxo-3-thiomorpholinylcarbonyl-L-histidyl-L-prolinamide was used as the compound of the present invention.

(1) Effects on passive avoidance response (1) Improving effect on scopolamine-induced amnesia:

After acquisition of passive avoidance response (acquisition trial), 0.5 mg/kg of scopolamine and the test drug were intraperitoneally administered to rats simultaneously. Fifteen minutes after, passiveavoidance response ( retrieval trial) was tested again. In the test described above, in the case that the compound of the present invention was orally administered as a test drug, the retrieval trial was performed one hour after the administration; in the case that TRH was orally administered as a test drug, the retrieval trial was performed 30 minutes after the administration. A rate of positive response (number of animals showing positive response/number of animals used) in each dose of the test drug is shown in Table 1.

TABLE 1

| No. | Test Drug | Route for Administration | Rate of Positive Response (number of animals showing positive response/number of animals used) Dose (mg/kg) | | | | |
|---|---|---|---|---|---|---|---|
| | | | — | 0.03 | 0.05 | 0.1 | 0.3 | 0.5 |
| (1) | Physiological saline | i.p. | 1/8 | | | | | |

TABLE 1-continued

| | | | | | | | |
|---|---|---|---|---|---|---|---|
| (2) | Compound of the invention | i.p. | | 2/8 | 5/8* | 6/8* | 5/8* | 4/8 |
| (3) | TRH | i.p. | | | | | | |
| (4) | Physiological saline | p.o. | 1/8 | | | | | |
| (5) | Compound of the invention | p.o. | | | | 1/8 | 4/8 | |
| (6) | TRH | p.o. | | | | | | |

| | Rate of Positive Response (number of animals showing positive response/number of animals used) Dose (mg/kg) | | | | | | |
|---|---|---|---|---|---|---|---|
| No. | 1 | 3 | 5 | 10 | 30 | 50 | 100 |
| (1) | | | | | | | |
| (2) | 1/8 | | | | | | |
| (3) | | | 1/8 | 3/8 | 0/8 | | |
| (4) | | | | | | | |
| (5) | 5/8* | 5/8* | | 4/8 | 2/8 | | |
| (6) | | | | | | 1/8 | 1/8 |

In Table 1, symbol * means that there is a significant difference at a probability of P<0.05 i.p. and p.o. mean intraperitoneal administration and oral administration, respectively (hereafter the same).

In the case of intraperitoneal administration, the compound of the present invention showed a significant improving effect in a dose range of 0.05 to 0.03 mg/kg but TRH showed no significant improving effect in a dose range (5-30 mg/kg) used. The compound of the present invention showed a significant improving effect in doses of 1 and 3 mg/kg even by oral administration but TRH showed no improving effect even by oral administration but TRH showed no improving effect even by oral administration in 50 to 100 mg/kg.

(2) Improving effect on electroshock-induced amnesia:

After an acquisition trial, electroshock was delivered to rats. After convulsion disappeared, the test drug was intraperitoneally administered and 15 minutes after, a retrieval trial was performed. The results are shown in Table 2.

TABLE 2

| | | Route for Administration | Rate of Positive Response (number of animals showing positive response/number of animals used) Dose (mg/kg) | | | |
|---|---|---|---|---|---|---|
| No. | Test Drug | | — | 0.1 | 0.3 | 0.5 |
| (1) | Physiological saline | i.p. | 0/8 | | | |
| (2) | Compound of the invention | i.p. | | | 2/8 | 5/8* | 4/8* |
| (3) | TRH | i.p. | | | | |

| | Rate of Positive Response (number of animals showing positive response/munber of animals used) Dose (mg/kg) | | | | | |
|---|---|---|---|---|---|---|
| No. | 1 | 2 | 3 | 5 | 10 | 30 |
| (1) | | | | | | |
| (2) | 4/8* | 2/8 | 2/8 | | | |
| (3) | | | 2/8 | 3/8 | 4/8* | 2/8 |

The compound of the present invention showed a significant improving effect in a dose range of 0.3 to 1 mg/kg but TRH showed a significant improving effect only in 10 mg/kg.

(3) Improving effect on cycloheximide-induced amnesia:

Immediately after an acquisition trial, 3 mg/kg of cycloheximide was subcutaneously administered to rats. Forty-eight hours after, a retrieval trial was performed. The test drug was intraperitoneally administered 15 minutes before the retrieval trial. The results are shown in Table 3.

TABLE 3

| | | Route for Administration | Rate of Positive Response (number of animals showing positive response/number of animals used) Dose (mg/kg) | | | | |
|---|---|---|---|---|---|---|---|
| No. | Test Drug | | — | 0.01 | 0.03 | 0.04 | 0.05 | 0.06 |
| (1) | Physiological saline | i.p. | 2/8 | | | | | |
| (2) | Compound of the invention | i.p. | | | 2/8 | 4/8 | 6/8* | 6/8* | 6/8* |
| (3) | TRH | i.p. | | | | | | |

| | Rate of Positive Response (number of animals showing positive response/number of animals used Dose (mg/kg) | | | | | | |
|---|---|---|---|---|---|---|---|
| No. | 0.08 | 0.1 | 0.3 | 1 | 3 | 5 | 10 | 30 |
| (1) | | | | | | | | |
| (2) | 6/8* | 2/8 | 2/8 | | | | | |
| (3) | | | | 3/8 | 3/8 | 2/8 | 2/8 | 1/8 |

The compound of the present invention showed a significant improving effect in a dose range of 0.04 to 0.08 mg/kg but TRH showed no significant improving effect in a dose range of 1 to 30 mg/kg.

(4) Improving effect on chloramphenicol-induced amnesia:

Immediately after an acquisition trial, 100 mg/kg of chloramphenicol and the test drug in each dose were intraperitoneally administered to rats at the same time. Twenty four hours after, a retrieval trial was performed. The results are shown in Table 4.

TABLE 4

| | | Route for Administration | Rate of Positive Response (number of animals showing positive response/number of animals used) Dose (mg/kg) | | | | |
|---|---|---|---|---|---|---|---|
| No. | Test Drug | | — | 0.03 | 0.05 | 0.1 | 0.3 | 0.5 |
| (1) | Physiological saline | i.p. | 3/8 | | | | | |
| (2) | Compound of the invention | i.p. | | | 4/8 | 8/8** | 7/8* | 7/8* | 7/8* |
| (3) | TRH | i.p. | | | | | | |

| | Rate of Positive Response Dose (mg/kg) | | | | |
|---|---|---|---|---|---|
| No. | 1 | 3 | 5 | 10 | 30 |
| (1) | | | | | |
| (2) | 7/8* | 7/8* | 4/8 | | |
| (3) | | | 4/8 | 3/8 | 4/8 |

In Table 4, symbol ** means that there is a significant difference at a probability of P<0.01 (hereafter the same).

The compound of the present invention showed a significant improving effect in a dose range of 0.05 to 3 mg/kg but TRH showed not significant improving effect in a dose range of 5 to 30 mg/kg.

(5) Improving effect on amnesia induced by lesion of the basal forebrain nucleus:

Rats in which the bilateral basal forebrain nucleus was electrically lesioned were used. The test drug and TRH were administered 15 and 3 minutes before an acquisition trial, respectively. Fifteen minutes after the acquisition trial, a retrieval trial was performed. The results are shown in Table 5.

TABLE 5

| No. | Test Drug | Route for Administration | Rate of Positive Response (number of animals showing positive response/number of animals used) Dose (mg/kg) | | | | | |
|---|---|---|---|---|---|---|---|---|
| | | | — | 0.01 | 0.03 | 0.05 | 0.1 | 0.3 |
| (1) | Physiological saline | i.p. | 2/8 | | | | | |
| (2) | Compound of the invention | i.p. | | 3/8 | 5/8 | 6/8* | 7/8* | 7/8* |
| (3) | TRH | i.p. | | | | | | |

| | Rate of Positive Response Dose (mg/kg) | | | | |
|---|---|---|---|---|---|
| No. | 0.5 | 1 | 5 | 10 | 30 |
| (1) | | | | | |
| (2) | 6/8* | 2/8 | | | |
| (3) | | | 2/8 | 1/8 | 1/8 |

The compound of the present invention showed a significant improving effect in a dose range of 0.05 to 0.5 mg/kg but TRH showed not significant improving effect at all in a dose range of 5 to 30 mg/kg.

(2) Effects on active avoidance and escape response

Improving effect on hypercapnia-induced amnesia:

The test drug was intraperitoneally administered and 15 minutes after, the rats were placed in a chamber filled up with carbon dioxide for 12 seconds. Three minutes after, active avoidance and escape response was examined using a buzzer in a shuttle box as conditioned stimulus and a rate of positive response (number of animals showing positive response/number of animals used) in the 6th trial was determined. The results are shown in Table 6.

TABLE 6

| No. | Test Drug | Route for Administration | Rate of Positive Response (number of animals showing positive response/number of animals used) Dose (mg/kg) | | | | | |
|---|---|---|---|---|---|---|---|---|
| | | | — | 0.03 | 0.05 | 0.1 | 0.3 | 0.5 |
| (1) | Physiological saline | i.p. | 1/8 | | | | | |
| (2) | Compound of the invention | i.p. | | 3/8 | 4/8 | 5/8* | 6/8* | 6/8* |
| (3) | TRH | i.p. | | | | | | |

| | Rate of Positive Response Dose (mg/kg) | | | | |
|---|---|---|---|---|---|
| No. | 1 | 3 | 10 | 30 | 50 |
| (1) | | | | | |
| (2) | 7/8** | 5/8* | | | |
| (3) | | | 1/8 | 3/8 | 4/8 |

The compound of the present invention showed a significant improving effect in a dose range of 0.1 to 3 mg/kg but TRH showed no significant improving effect in a dose range of 10 to 50 mg/kg.

(3) Effects on the acquisition of conditioned avoidance response

Rats in which the bilateral basal forebrain nucleus was electrically lesioned were used. Conditional avoidance response was examined using a shuttle box. Rats were placed in the shuttle box. Thirteen seconds after, a buzzer was given for 3 seconds as conditioned stimulus and then an electric shock (unconditioned stimulus) was delivered for 4 seconds through a grid of the floor together with the buzzer. When the rats moved to another compartment within 3 seconds of the conditioned stimulus the unconditioned stimulus was avoided (positive in the conditioned avoidance response). 20 Trials were performed daily and a rate of conditioned avoidance response was determined. Tests for the conditioned avoidance response were started 7 days after the lesion of the basal forebrain nucleus and rats were trained following 9 days, rate of conditioned avoidance response on the last day of training is shown in Table 7.

TABLE 7

| No. | Test Drug | Route for Administration | Rate of Active Avoidance Response (%) Dose (mg/kg) | | |
|---|---|---|---|---|---|
| | | | — | 0.05 | 0.1 | 0.3 |
| (1) | Physiological saline | i.p. | 59.5 ± 5.9 | | | |
| (2) | Compound of the invention | i.p. | | 74.5 ± 4.8 | 82.5** ± 4.0 | ± 3.1 |
| (3) | TRH | i.p. | | | | |

| | Rate of Evasion Response (%) Dose (mg/kg) | | | | |
|---|---|---|---|---|---|
| No. | 0.5 | 1 | 5 | 10 | 30 |
| (1) | | | | | |
| (2) | 81.4** ± 3.6 | 86.1** ± 2.9 | | | |
| (3) | | | 72.0 ± 6.6 | 91.4** ± 1.4 | 66.3 ± 6.0 |

The compound of the present invention showed a significant increase in the acquisition of active avoidance response in a dose range of 0.1 to 1 mg/kg but TRH showed a significant effect only in the 10 mg/kg.

(4) Effects on radial maze task

A radial maze having 8 arms radiating in all directions was used. A small piece of cheese was placed as a reward in the well of the end of each arm. Starved rats were placed on the center platform of the radial maze and allowed to make free access to the reward placed in the end of the arm but the rewards were placed in the well so that the rats at the center of the maze could not see them. In this test, the case that the rat chose an arm on which the reward was placed was judged to be correct choice. Training was made until the number of correct choice reached at least 7 and continued for 3 days or more.

Using animals satisfying such a criterion, an improving effect of the test drug on the impairment of the radial maze task induced by scopolamine was examined. The test was conducted 30 minutes after intraperitoneal administration of scopolamine in a dose of 0.3 mg/kg. The compound of the present invention, TRH and physostigmine were intraperitoneally administered 15, 10 and 15 minutes before the test, respectively. When the compound of the present invention was orally administered, it was treated one hour prior to the test. The results are shown in Table 8.

TABLE 8

| Test No. | Drug | Route for Administration | Number of Correct Choice Dose (mg/kg) | | | |
|---|---|---|---|---|---|---|
| | | | — | 0.03 | 0.1 | 0.3 |
| (1) | Physiological saline | i.p. | 6.42 ±0.26 | | | |
| (2) | Compound of the invention | i.p. | | 6.83 ±0.31 | 6.83 ±0.17 | 7.80** ±0.20 |
| (3) | TRH | i.p. | | | | |
| (4) | PH | i.p. | | | | 6.75 ±0.25 |
| (5) | Physiological saline | p.o. p.o. | 5.90 ±0.23 | | | |
| (6) | Compound of the invention | p.o. p.o. | | | | 6.5 ±0.27 |

| No. | Number of Correct Choice Dose (mg/kg) | | | | | |
|---|---|---|---|---|---|---|
| | 0.5 | 1 | 3 | 5 | 10 | 30 |
| (1) | | | | | | |
| (2) | 6.20 ±0.20 | | | | | |
| (3) | | | 6.50 ±0.29 | 7.00 ±0.32 | 7.00 ±0.45 | 7.00 ±0.45 |
| (4) | 7.50* ±0.22 | 7.17 ±0.48 | | | | |
| (5) | | | | | | |
| (6) | | 6.80* ±0.29 | 6.10 ±0.23 | | | |

The compound of the present invention showed a significant improving effect by intraperitoneal administration in a dose of 0.3 mg/kg and by oral administration in a dose of 1 mg/kg but TRH showed no significant improving effect in any dose by intraperitoneal administration of 3 to 30 mg/kg. Physostigmine (represetned by PH in Table 8) showed a significant improving effect by intraperitoneal administration in a dose of 0.5 mg/kg.

(5) Effects on the delayed non-matching to sample task:

A T-shaped maze was used. An apparatus was comprised of a starting box, a running path and goal boxes, each being provided with a guillotine door at an inlet and outlet.

One trial of this task comprises two runs of forced and choice runs. In the forced run, a guillotine door of one of the left and right goal boxes is closed so that a starved rat can enter into one goal box. When a rat enters into a goal box with an opened guillotine door, a reward (a small piece of cheese) is given to the rat. Immediately thereafter, the rat is brought back to the starting box with a closed guillotine door. After a delay time for 5 seconds, a choice run was made. In the selective running, the rat can enter into both of the goal boxes but a reward is given only when the rat chooses a goal box different from a box where a reward was given in the forced run.

Rats were trained 6 trials a day until the rat took correct choice in at least 5 trials in daily sessions and for consecutive 3 days.

Using the rats trained to satisfy the criterion, an improving effect of the test drug on the impairment of the task induced by scopolamine was examined. The test was comprised of 4 trials with trials in delayed Lime of 5, 30, 120 and 480 seconds. The delayed time was one trial each at random. Scopolamine(0.3 mg/kg) was intraperitoneally administered 20 minutes before the test and the compound of the present invention and physostigmine (PH) were intraperitoneally administered 5 minutes before the test, respectively. The results are shown in Table 9.

TABLE 9

| Test No. | Drug | Route for Administration | Dose (mg/kg) | Number of Correct Choice (%) | | | |
|---|---|---|---|---|---|---|---|
| | | | | 5 | 30 | 120 | 480 (sec) |
| (1) | Physiological saline | i.p. | — | 70.0 ±4.1 | 58.3 ±6.3 | 45.0 ±5.0 | 45.0 ±3.6 |
| (2) | Compound of the invention | i.p. | 0.3 | 90.0** ±5.1 | 76.7* ±5.1 | 73.3** ±8.3 | 66.7** ±7.0 |
| (3) | PH | i.p. | 0.5 | 90.0** ±5.1 | 66.7 ±9.9 | 53.3 ±10.2 | 46.7 ±5.4 |

The compound of the present invention in a dose of 0.3 mg/kg significantly improved the impairment of the task induced by 0.3 mg/kg of scopolamine in delayed time of 5, 30, 120 and 480 seconds but physostigmine showed a significant improving effect only in delayed time of 5 seconds in a dose of 0.5 mg/kg.

According to the test examples (1) to (5) above, effectiveness of the compound of the present invention is apparent and its effectiveness is clearly exhibited not only by injection (intravenous injection, drop intravenous injection, subcutaneous injection, intramuscular injection), topical administration (intrarectal, sublingual, intranasal and so on) but also by oral administration.

(6) Acute toxicity

After intravenous administration and oral administration of the compound of the present invention to male mice, toxic behaviors were observed for 7 days.

Neither death nor toxic behavior was observed by intravenous administration of the compound of the present invention in a dose of 1000 mg/kg. In the case of oral administration of the compound of the present invention, either death nor toxic behavior was observed in a dose of 5000 mg/kg.

Safety of the compound of the present invention was evident.

INDUSTRIAL APPLICABILITY

In the case of administering the compounds of the present invention as drugs, the compounds of the present invention are administered to animals including human as they are or as drug compositions containing in a pharmaceutically acceptable non-toxic inert carrier, for example, 0.0001 to 1.2% as an injection, 0.0001 to 2% as a tablet, preferably 0.01 to 1% as an injection and 0.001 to 1% as a tablet.

As the carrier, at least one of a solid, semi-solid or liquid diluent, filler and other pharmaceutical auxiliary agents may be used. The pharmaceutical composition is desirably administered in a dose unit form. The pharmaceutical composition of the present invention can be administered orally, in tissue, topically (subcutaneous administration, etc.) or intrarectally. The compounds of the present invention are administered in preparations suited for these administration methods, of course. For example, oral administration is particularly preferred.

Dosage as a nootropic agent may be desirably adjusted depending upon condition of the patient such as age, body weight, etc., route for administration, property and severity of disease, etc. The compounds of the present invention are administered to adult generally in a daily dose ranging from 0.01 to 50 mg, preferably 0.1 to 10 mg, as an effective ingredient of the present invention. Depending upon the situation, the dose may be smaller or conversely larger than the range. It is also desired that the compounds of the present invention are administered in several portions a day.

Oral administration can be effective by a solid or liquid dosage unit, for example, powdered drugs, powders, tablets, coated tablets, capsules, granules, suspensions, liquid, syrup, drop, troche and other preparation forms.

The powdered drugs can be prepared by pulverizing the active substance into suitable fineness. The powders can be prepared by pulverizing the active substance into suitable fineness and then mixing with finely pulverized pharmaceutical carriers, for example, edible carbohydrates such as starch, mannitol, etc. and others. If necessary, flavors, preservatives, dispersing agents, coloring agents, fragrance may also be mixed.

The capsules can be prepared by encapsulating the powdered drug as described above or powders or granules as described with tablets into capsule coating such as gelatin capsule. Further a lubricant or fluidizing agent, for example, colloidal silica, talc, magnesium stearate, calcium stearate or solid polyethylene glycol, may be mixed with the powdery drug followed by encapsulation. When a disintegrator or solubilizing agent, for example, carboxymethyl cellulose, carboxymethyl cellulose calcium, hydroxypropyl cellulose having a low substitution degree, calcium carbonate or sodium carbonate is incorporated, effectiveness of the drug when the capsule is taken can be improved.

Furthermore, the fine powders of the active substance may be suspended and dispersed in vegetable oil, polyethylene glycol, glycerine or surface active agent and the dispersion can be coated to a gelatin sheet to make a soft capsule. The tablets can be prepared by preparing a powdery mixture, converting the mixture into granules or slugs, then adding a disintegrator or lubricant thereto and tableting. The powdery mixture can be prepared by mixing a suitably pulverized substance with the aforesaid diluent or base, if necessary, may also be used in combination with a binder (for example, sodium carboxymethyl cellulose, alginates, gelatin, polyvinylpyrrolidone, polyvinyl alcohol, etc.), a dissolution retarder (for example, paraffin, etc.), a reabsorbing agent (for example, a quaternary salt) or an adsorbing agent (for example, bentonite, kaolin, dicalcium phosphate, etc.). The powdery mixture is firstly wetted with a binder such as a syrup, a starch glue, gum arabic, a cellulose solution or high molecular substance solution and then forcedly passing through a sieve to convert into granules. Instead of converting powders into granules as described above, it may also be possible to firstly subjecting to a tableting machine and then grinding the obtained slugs in an incomplete shape into granules.

The thus prepared granules can be prevented from being adhered to each other by adding thereto stearic acid, stearates, talc, mineral oil, etc. as a lubricant. The thus lubricated mixture is then tableted. In addition, the drug may also be mixed with a fluidizable inert carrier and then directly tableted, without steps of granulating or making into slugs. A transparent or semi-transparent protective coating composed of a shellac-sealed coating, a coating with sugar or high molecular materials and a polished coating composed of wax, etc. can also be used.

Other oral administration preparations, for example, a solution, a syrup, an elixir, etc. may also be prepared into a dose unit form so as to contain a definite dose of the drug in its definite amount. The syrup can be prepared by dissolving the compound in a suitably flavoured aqueous solution. The elixir can be prepared using a non-toxic alcoholic carrier. The suspension can be prepared by dispersing the compound into a non-toxic carrier. A solubilizing agent or emulsifying agent (for example, ethoxylated isostearyl alcohols, polyoxyethylene sorbitol esters), a preservative, a flavor imparting agent (for example, peppermint oil, saccharin) and others may also be added, if necessary.

If desired, a dose unit formulation for oral administration may also be microencapsulated. This formulation can achieve delay in acting time or durative release by coating or embedding into high molecular substance or wax, etc.

Parenteral administration can be effected by using a liquid dose unit form for example, a solution or a suspension which is used as a subcutaneous, intramuscular or intravenous injection. These injections can be prepared by suspending or dissolving a definite amount of the compound in a non-toxic liquid carrier suited for injection purpose, for example, an aqueous or oily medium and then sterilizing the suspension or solution. Alternatively, a definite amount of the compound is taken in a vial and then the vial and its content are sterilized and sealed. For dissolving or mixing immediately before administration, a preliminary vial or carrier may also be prepared together with powders or freeze-dried powders of the effective ingredient. In order to render an injection isotonic, a non-toxic salt or salt solution may also be added. In addition, a stabilizer, a preservative or an emulsifier, etc. may also be used in combination.

Rectal administration can be effective by using a suppository obtained by mixing the compound with a low melting water-soluble or water-insoluble solid, for example, polyethylene glycol, cacao fat, higher esters (for example, myristyl palmitate) and a mixture thereof.

For making preparations of the compounds of the present invention, other drugs, for example, other antacid agent, a histamin $H_2$-antagonist, etc. may also be used in addition to the effective ingredient in accordance with the present invention.

BEST MODE FOR PRACTICING THE INVENTION

Hereafter the present invention is described in more detail, by referring to formulation examples of the present invention.

Formulation 1

Taking 4 mg of (3R,6R)-6-methyl-5-oxo-3-thiomorpholinyl-carbonyl-L-histidyl-L-prolinamide, 50 mg of lactose, 22 mg of corn starch, 5.1 mg of crystalline cellulose, 3.4 mg of hydroxypropyl cellulose and 0.5 mg of magnesium stearate per tablet, a tablet was prepared in a conventional manner.

Formulation 2

Taking 4 mg of (3R,6R)-6-methyl-5-oxo-3-thiomorpholinyl-carbonyl-L-histidyl-L-prolinamide, 335 mg of lactose, 144.5 mg of corn starch, 1.5 mg of hydrated silicon dioxide and 15 mg of hydroxypropyl cellulose per tablet, a fine granule was prepared in a conventional manner.

We claim:

1. A method for effecting nootropic action in humans and animals which comprises administering to a human or animal in need thereof a therapeutically effective amount of a compound of the formula (I):

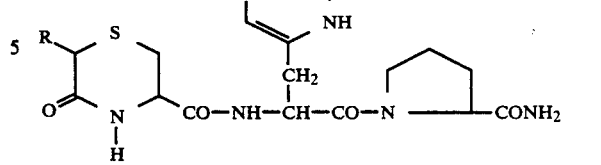

wherein R is lower alkyl, in combination with a pharmaceutically acceptable carrier.

2. A method according to claim 1 wherein the compound is 6-methyl-5-oxo-3-thiomorpholinylcarbonyl-histidylprolinamide.

3. A method according to claim 1 wherein the compound is 6-methyl-5-oxo-3-thiomorpholinylcarbonyl-histidylprolinamide.

4. A method according to claim 1 wherein the compound is 6-methyl-5-oxo-3-thiomorpholinylcarbonyl-histidylprolinamide.

5. A method according to claim 1 wherein the compound is (3R, 6R)-6-methyl-5-oxo-3-thiomorpholinyl-carbonyl-L-histidyl-L-prolinamide.

6. A method according to claim 1 wherein the administration is oral.

7. A method according to claim 1 which comprises administering to a human or animal in need thereof a therapeutically effective amount of a compound of the formula (I), in combination with a pharmaceutically acceptable carrier in unit dosage form.

8. A method according to claim 1 wherein the therapeutically effective amount is from about 0.0 mg to about 50 mg per day for a human adult.

* * * * *